United States Patent [19]

Say et al.

[11] 4,065,381

[45] Dec. 27, 1977

[54] MAINTAINING EFFECTIVE MOLAR RATIO OF HF TO METAL PENTAFLUORIDE IN A HYDROCARBON CONVERSION PROCESS

[75] Inventors: Geoffrey R. Say; William C. Baird, Jr.; Paul W. Kamienski, all of Baton Rouge, La.

[73] Assignee: Exxon Research and Engineering Company, Linden, N.J.

[21] Appl. No.: 758,053

[22] Filed: Dec. 29, 1976

[51] Int. Cl.$^2$ .......................... C07C 5/28; C07C 9/00; C07C 3/12; C10G 35/06
[52] U.S. Cl. ............................. 208/134; 260/666 P; 260/672 T; 260/676 R; 260/683.47; 260/683.68
[58] Field of Search .................. 260/683.68, 683.47, 260/683.51, 666 P, 671 R, 671 C, 672 T, 668 R, 683.9, 676 R; 208/134, 108, 64

[56] References Cited

U.S. PATENT DOCUMENTS

| | | | |
|---|---|---|---|
| 2,683,763 | 7/1954 | Lien et al. | 260/672 T |
| 2,683,764 | 7/1954 | Lien et al. | 260/672 T |
| 3,728,411 | 4/1973 | Siskin et al. | 260/668 R |
| 3,809,728 | 5/1974 | Kemp et al. | 260/683.68 |
| 3,852,184 | 12/1974 | Siskin et al. | 208/64 |
| 3,888,937 | 6/1975 | Siskin et al. | 260/683.9 |
| 3,901,790 | 8/1975 | Siskin et al. | 208/108 |
| 3,948,761 | 4/1976 | Siskin et al. | 260/666 P |
| 4,025,577 | 5/1977 | Siskin et al. | 260/683.47 |

*Primary Examiner*—George Crasanakis
*Attorney, Agent, or Firm*—John W. Ditsler

[57] ABSTRACT

A hydrocarbon phase separated from a hydrocarbon conversion process is solvent extracted with anhydrous liquid HF to separate metal pentafluoride which is carried over into the hydrocarbon phase. The extract of HF and metal fluoride is then combined with the catalyst phase (HF and metal pentafluoride) and stripped with hydrogen to reduce the molar ratio of HF to metal pentafluoride to the level that HF + metal pentafluoride catalyst is utilized in the hydrocarbon conversion process. The metal pentafluoride is TaF$_5$ and/or NbF$_5$ and the hydrocarbon conversion may involve isomerization, alkylation with olefins and reactions of a paraffin with another paraffin.

9 Claims, 1 Drawing Figure

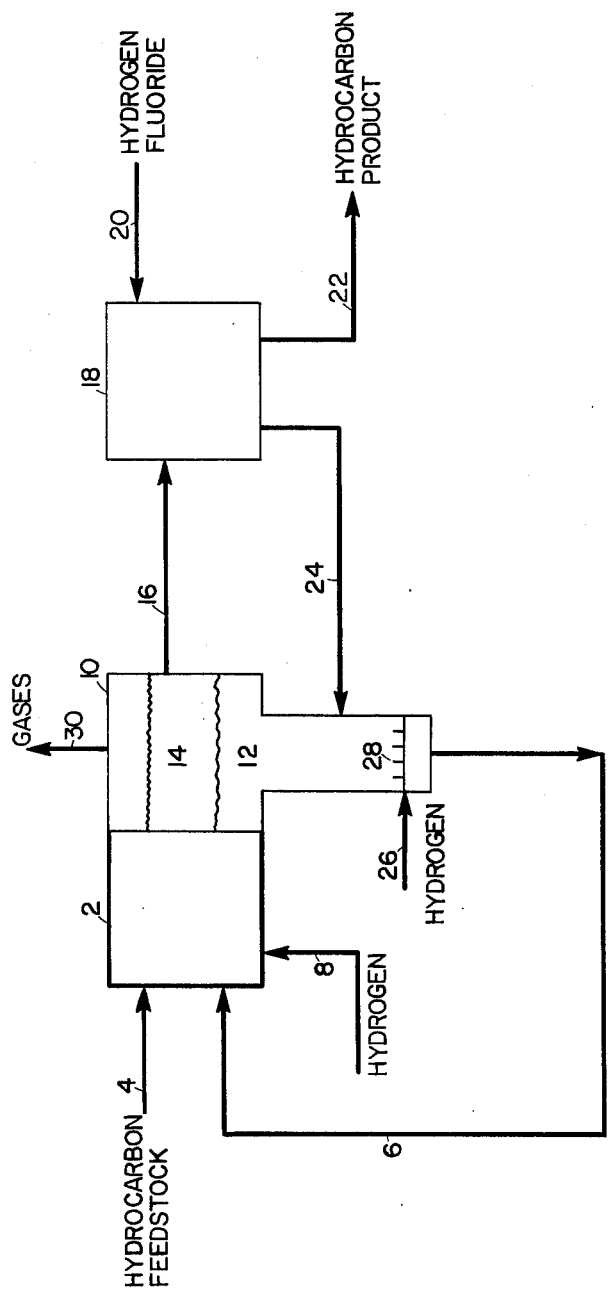

MAINTAINING EFFECTIVE MOLAR RATIO OF HF TO METAL PENTAFLUORIDE IN A HYDROCARBON CONVERSION PROCESS

BACKGROUND OF THE INVENTION

1. Field of the Invention

The present invention relates, in general, to hydrocarbon conversion processes. More particularly, this invention relates to a hydrocarbon conversion process, which employs a catalyst comprising a metal pentafluoride and hydrogen fluoride, wherein the molar ratio of hydrogen fluoride to metal pentafluoride in a stream obtained from recovering minor amounts of metal pentafluoride from the hydrocarbon effluent from said process is maintained at the ratio desired in said process.

2. Description of the Prior Art

The liquid phase strong acid catalyst system comprising (a) a metal pentafluoride selected from the group of tantalum pentafluoride, niobium pentafluoride and mixtures thereof and (b) hydrogen fluoride is known to be useful in promoting various hydrocarbon conversion reactions (see, for example, U.S. Pat. Nos. 2,683,763; 2,683,764; 3,728,411; 3,852,184; 3,888,937; 3,901,790; 3,948,761; as well as application Ser. No. 586,176, filed June 12, 1975, which issued as U.S. Pat. No. 4,025,577 on May 24, 1977, the disclosures of which were incorporated herein by reference). These reactions include isomerization, alkylation, disproportionation, naphthene cleavage, aromatic hydrogenation, and the like.

Generally, in such conversion reactions, the conversion zone effluent is subsequently separated by settling into two phases, namely, a predominantly hydrocarbon phase and a predominantly acid catalyst phase. Although the major portion of the metal pentafluoride that was present in the conversion zone effluent settles in the acid phase, a minor but significant amount of the metal pentafluoride along with some hydrogen fluoride is carried over into the hydrocarbon phase. The concentration of the metal pentafluoride in such hydrocarbon streams typically ranges from about 5 to 10,000 wppm. Although the amount of metal pentafluoride in the hydrocarbon stream may be small, its presence results in numerous difficulties in the process equipment, e.g., fouling and corrosion of the equipment. Furthermore, the loss of these amounts of metal pentafluoride represents a considerable economic disadvantage since fresh metal pentafluoride would have to be added to the system to compensate for that discharged in the hydrocarbon. Thus the recovery of the trace amounts of metal pentafluoride from the hydrocarbon phase for reuse as catalyst would have both economic and process benefits.

One method of recovering the metal pentafluoride is disclosed in U.S. Pat. No. 3,830,870, the disclosures of which are incorporated herein by reference. According to this method, a hydrocarbon stream containing minor amounts of metal pentafluoride is contacted with substantially anhydrous liquid hydrogen fluoride such that there is formed an extract phase containing predominantly hydrogen fluoride and at least a portion of the metal pentafluoride thus removed. Typically, the mole ratio of hydrogen fluoride to metal pentafluoride is more than 100:1. However, it is known that the effectiveness of this catalyst system in hydrocarbon conversion processes is related to the molar ratio of hydrogen fluoride to said metal pentafluoride. More particularly, in order to maximize catalyst activity and activity maintenance, it is desirable to operate said processes at a catalyst composition wherein the molar ratio of HF to metal pentafluoride is at least equal molar, preferably at least 5, more preferably at least 10, but less than 40. Most preferably, the molar ratio is maintained within the range of from 5 to 40.

One method for adjusting the molar ratio of HF to metal pentafluoride in the extract phase is to remove a portion of the hydrogen fluoride by distillation as described in the patent. However, this method requires expenditures for the separate distillation zone. Thus, it would be highly desirable to have available a simple and convenient method of adjusting the molar ratio of hydrogen fluoride to metal pentafluoride in the extract phase to the level desired in hydrocarbon conversion process which does not involve the necessity of additional equipment other than that normally employed in said process.

SUMMARY OF THE INVENTION

Now according to the present invention, a simple and convenient method has been discovered for adjusting the molar ratio of hydrogen fluoride to metal pentafluoride in at least a portion of the extract phase formed during the recovery of metal pentafluoride from the hydrocarbon phase effluent of a hydrocarbon conversion process, said process employing a catalyst comprising hydrogen fluoride and a metal pentafluoride, to the molar ratio desired in said conversion process. This may be effected by combining the extract phase thus formed with the catalyst effluent from the hydrocarbon conversion process and contacting same with a gas containing molecular hydrogen for a time sufficient to reduce the molar ratio of hydrogen fluoride to metal pentafluoride in the combined stream to the level desired in said hydrocarbon conversion process. At least a portion, preferably a major portion, of the stripped catalyst may then be returned to said hydrocarbon conversion process. Hydrogen, in addition to serving as a stripping medium, serves to inhibit catalyst deactivation. In a preferred embodiment, the hydrogen stripping is effected in the settling zone of said hydrobarbon conversion process.

BRIEF DESCRIPTION OF THE DRAWING

The single FIGURE is a diagrammatic representation of one embodiment of the present invention.

DETAILED DESCRIPTION OF THE INVENTION

Having thus described the invention in general terms, reference is now made to the FIGURE which shows one embodiment thereof. Such details are included as are necessary for a clear understanding of how the present invention may be employed. No intention is made to unduly limit the scope of the present invention to the particular configuration shown as variations are obvious to those having ordinary skill in the art of hydrocarbon conversion processes and are included within the broad scope of the present invention.

Referring now to the FIGURE, there is shown a hydrocarbon conversion reaction zone 2, into which a hydrocarbon feedstock is being introduced via line 4 to be contacted with a hydrocarbon conversion catalyst introduced via line 6, said catalyst comprising (a) a metal pentafluoride selected from the group consisting of tantalum pentafluoride, niobium pentafluoride and mixtures thereof, and (b) hydrogen fluoride. A wide variety of hydrocarbon conversion reactions may be effected within said hydrocarbon conversion zone, including those that occur under the influence of Friedel-Crafts type catalysts, e.g., isomerization, alkylation, polymerization, cracking, hydrogenation, disproportionation, and the like. Similarly, the feedstocks employed will be those corresponding with the particular hydrocarbon conversion reaction occurring within zone 2. Typically, the feedstocks used in such processes will contain hydrocarbons containing from about 1 to about 20 carbon atoms and will have a 50% boiling point below 230° C., preferably below 205° C., measured at atmospheric pressure. Similarly, the particular temperatures and pressures employed in zone 2 will vary with the reaction being conducted therein. However, temperatures will generally be in the range of from about 0° to about 150° C. with total pressures ranging from about 1 to about 100 atmospheres. Molecular hydrogen may or may not be necessary depending upon the requirements of the particular hydrocarbon conversion process. Preferably, however, hydrogen will be present and is shown in the FIGURE as being introduced into zone 2 via line 8.

As noted above, the effectiveness of the catalyst system employed herein for hydrocarbon conversion reactions is related to the molar ratio of hydrogen fluoride to metal pentafluoride. The catalyst should be prepared such that at least an equal molar amount of hydrogen fluoride relative to metal pentafluoride is present in the reaction zone. Preferably, the molar ratio should be maintained between about 1 and 40, more preferably between 5 and 40, and most preferably between 10 and 40.

After allowing sufficient residence time for the reaction to progress, typically, in the order from about 1 minute to about 1 hour or more, the hydrocarbon-catalyst mixture formed in said hydrocarbon conversion zone 2, often referred to as an "emulsion mixture", is then passed into settling zone 10. The emulsion mixture will separate in settling zone 10 into a predominantly heavier catalyst phase 12 (which is located in the lower portion of zone 10) containing a major portion of the metal pentafluoride present in the effluent from said conversion zone and into a predominantly lighter hydrocarbon phase 14 containing hydrocarbon product along with minor amounts of metal pentafluoride dissolved and/or entrained therein. Typically, the dissolved and/or entrained metal pentafluoride amounts to about 5 to about 10,000 wppm of the total hydrocarbon phase. The predominantly hydrocarbon phase containing trace amounts of metal pentafluoride is removed via line 16 and introduced into extraction zone 18 and contacted countercurrently therein with a solvent stream of substantially anhydrous liquid hydrogen fluoride introduced via line 20. By substantially anhydrous is meant liquid hydrogen fluoride that does not contain more than about 0.5 wt.% preferably 0.2 wt.% water.

The extraction zone can be any conventional tower or column suitable for conducting countercurrent liquid-liquid extractions. The tower can be packed with HF-resistant contact materials such as Raschig rings, Berl saddles, etc. The extraction step, may, for example, be conducted in a multi stage, countercurrent mixing-settling vessel, plate tower, stirred tank reactor to produce a mixture which is subsequently allowed to settle and separate into two phases.

The extraction is conducted at a temperature in the range of from about 0° to about 100° C., preferably in the range from about 20° to 60° C., and more preferably at about 25° C. and at a pressure in the range of about 1 to about 15 atmospheres. A volume ratio total treating solvent to hydrocarbon phase may range from about 1:200 to 1:1, preferably from about 1:100 to 1:5, more preferably at a solvent to hydrocarbon phase ratio of about 1:20.

Contact of the hydrogen fluoride solvent with the hydrocarbon product preferentially extracts the metal pentafluoride into said solvent. The thus extracted hydrocarbon product having a reduced metal pentafluoride content (the raffinate) is removed from the extraction zone via line 22. At least a portion, preferably a major portion, more preferably all of the extract phase comprising predominantly hydrogen fluoride, along with some hydrocarbon product and the metal pentafluoride removed from the hydrocarbon product stream, is then passed via line 24 into the lower portion of settling zone 10. The molar ratio of hydrogen fluoride to metal pentafluoride normally will be more than 40, usually at least 100 or more.

According to the embodiment shown in the FIGURE, the extract phase is concentrated in the settling zone 10 by stripping HF therefrom using a gaseous stream containing molecular hydrogen which is introduced via line 26. The rate of flow of stripping gas is set to obtain the HF to metal pentafluoride molar ratio that is desired in the reaction zone 2. Thus, the molar ratio of HF to the metal pentafluoride of catalyst stream leaving settling zone 10 via line 6 is less than the HF to the metal pentafluoride molar ratio of the extract phase leaving extracting zone 18. The catalyst withdrawn from settler 10 may then be recycled to the hydrocarbon conversion zone.

Surprisingly, it has been discovered that hydrogen stripping in the settling zone, i.e. the movement of gas therein, can be effected without disturbing the separation of hydrocarbon phase 14 and catalyst phase 12. The hydrogen contacting in settling zone 10 may be effected using gentle hydrogen sparging. This will not only provide the necessary HF stripping to adjust the molar ratio of hydrogen fluoride to metal pentafluoride to the level desired in the hydrocarbon conversion process, but will also serve to inhibit deactivation of the catalyst phase 12, which would be more pronounced in the absence of the hydrogen. The hydrogen injection system may comprise a gas distributor 28 at the bottom of the settling zone 10. The hydrogen contacting in the settler could also be accomplished using a draft tube arrangement in order to reduce any turbulence due to the motion of the hydrogen bubbles. Thus, according to the present invention the settling will not be disturbed by the gentle agitation of the rising hydrogen bubbles. Any gases present in the system at this point, will disengage and pass from the settling zone via line 30. If desired hydrogen fluoride in the gas may be recovered and recycled to zone 18 via line 20.

As noted above, the present invention is applicable to a wide variety of reactions that occur under the influence of Friedel-Crafts catalysts. It is, however, particularly applicable to isomerization and alkylation reactions. Typical isomerizable feedstocks include acyclic and alicyclic aliphatic hydrocarbons having at least four carbon atoms that are converted to a product enriched in an isomer thereof. Typically, acyclic hydrocarbons having at least four carbon atoms, that is straight chain or branched chain paraffins having from about 4 to 20 carbon atoms, preferably from about 4 to 12 carbon atoms, are converted to branched materials having higher octane ratings. Additionally, alicyclic hydrocarbons (naphthenes) having at least 6 carbon atoms, typically from 6 to about 20 carbon atoms, preferably 6 to 15 carbon atoms, can be converted to isomers thereof by contacting the same with hydrogen in the presence of the catalyst system described previously. Mixtures of acyclic and alicyclic hydrocarbons can be used as the process feedstock. In a typical commercial operation, a paraffin stream containing mixtures of various types of open chain and closed chain paraffins is used as the process feedstock. Typical isomerization reaction conditions are summarized below.

| Range | Suitable | Preferred |
|---|---|---|
| Temperature, °C | 0 – 150 | 30 – 75 |
| Hydrogen Partial Pressure, atm. | 0.1 – 140 | 0.3 – 25 |
| Reaction Time, min | 0.5 – 1500 | 1 – 500 |
| Moles H$_2$/Mole Hydrocarbon | 0.01 – 2.5 | 0.1 – 1.0 |
| Space Velocity V/Hr./V | 0.05 – 200 | 0.25 – 50 |

In the alkylation of hydrocarbons with olefins, suitable olefinic starting materials are ethylene, propylene, butylenes, trimethyl ethylene and other isomeric pentenes, and similar higher monoolefinic hydrocarbons of either a straight chain or branched chain structure. Olefins containing 2 to about 12 carbon atoms per molecule are preferred while olefins containing 2 to 5 carbon atoms per molecule are particularly preferred. The reaction mixtures may also contain some amounts of diolefins. Although it is desirable from an economic viewpoint to use the normally gaseous olefins as reactants, normally liquid olefins may also be used. Thus, polymers, copolymers, interpolymers, crosspolymers, etc., of the above-mentioned olefins, as for example, propylene dimer, the diisobutylene and triisobutylene polymers, the codimer of normal and isobutylenes and the like may be used. The use of mixtures of two or more of the above-described olefins is also envisioned for this purpose.

Hydrocarbon feedstocks that are suitable for use in alkylation processes include paraffins, aromatic alkyl substituted aromatic hydrocarbons and mixtures thereof. The paraffins as herein defined include the acyclic and alicyclic hydrocarbons. The acyclic hydrocarbons (straight and branched chain materials) contain at least 1, preferably 1 to about 12 carbon atoms per molecule, and may be exemplified by methane, ethane, propane, butanes, methylbutanes, n-pentane, methylpentanes, methylhexanes, and the like. The alicyclic hydrocarbon (naphthenes) contain at least 5, typically from 5 to about 15 carbon atoms per molecule, preferably 6 to 12 carbon atoms and may be exemplified by methylcyclopentane, dimethylcyclopentane, methylcyclohexane, ethylcyclohexane, n-pentylcyclohexane and the like. Useful aromatic and alkyl aromatic hydrocarbons contain at least 6, preferably 6 to about 20 carbon atoms per molecule, and are exemplified by benzene, ethyl benzene, n-butyl benzene and the like. Other acyclic or alicyclic hydrocarbons commonly found in conventional petroleum hydrocarbon light naphtha streams and the like may be present. Typical alkylation reaction conditions are summarized below:

| Range | Suitable | Preferred |
|---|---|---|
| Temperature, °C | −100 – +150 | −10 – +80 |
| Hydrogen Partial Pressure, atm. | 0.1 – 100 | 0.3 – 25 |
| Reaction Time, min. | 0.001 – 60+ | 0.001 – 45 |
| Space Velocity based on olefin, V/Hr./V | 0.01 – 10 | 0.04 – 5 |

A paraffin can also be alkylated with another paraffin using the catalyst system described herein. For example, a paraffinic feedstock comprising a member selected from the group consisting of iC$_4$-C$_6$ aliphatic hydrocarbons, C$_5$–C$_{15}$ cycloaliphatic hydrocarbons and mixtures thereof can be alkylated with larger paraffins, i.e. paraffins or a mixture of paraffins having more than 6 carbon atoms, to form lower molecular weight materials. More specifically, a paraffinic feedstock containing smaller paraffins, i.e. isobutane, isopentanes, isohexanes or mixtures thereof, can undergo alkylation with larger paraffins to form lower molecular weight hydrocarbons. Thus, isobutane can undergo a paraffin alkylation reaction with a heptane to form pentanes and hexanes. The conditions employed are the same as those shown in the preceding table. However, hydrogen may or may not be present. It is preferred that all of the above-mentioned hydrocarbon conversion processes be conducted under substantially anhydrous conditions, i.e. less than 0.5 wt.% water.

The following example is presented to further illustrate the present invention and is not intended to unduly restrict the limits of the claims appended hereto:

A hexane feedstock containing 2–3 wt.% benzene was introduced into a 9 inch long horizontally disposed carbon steel reactor (I.D-12 inches) and contacted therein with an HF/TaF$_5$ catalyst, the HF/TaF$_5$ mole ratio being about 10:1. The catalyst to oil volume ratio was 1:2. The reactor was equipped with a 7 inch flat bladed turbine (six blades) to provide agitation in the system. The reactor also contained three sapphire windows for visual observations. A series of runs were made in which the hydrocarbon and catalyst were first agitated at mixing speeds ranging from 120 to 180 rpm to form an emulsion mixture. Agitation was stopped and the mixture allowed to settle into an upper hydrocarbon phase and a lower catalyst phase. The time required to effect the separation such that there was a visually observed clear boundary layer between the two phases, i.e. from the time the mixer was switched off until the two layers had totally disengaged, was measured. Agitation was then resumed and the procedure repeated a number of times. A series of runs was made at 122° F and 100 psig without hydrogen addition. Another series of runs was made in the same reactor using the same reactants, under the same conditions and following the same procedure with hydrogen, the hydrogen being introduced continuously into the bottom of the reactor at a rate of 62 SCF/hr. and in such a manner as to be distributed across the bottom of the reactor. The results of these runs are compared below:

| Hydrogen stripping Run No. | Settling Time | |
|---|---|---|
| | No | Yes |
| 1 | 25 | 24 |
| 2 | 24 | 25 |
| 3 | 21 | 26 |
| 4 | 21 | 25 |

The results show that passing hydrogen into the settling emulsion has no effect on settling time.

What is claimed is:

1. In a hydrocarbon conversion process which comprises
   1. converting a hydrocarbon feedstock with a substantially liquid phase acid catalyst comprising (a) a metal pentafluoride selected from the group consisting of tantalum pentafluoride, niobium pentafluoride and mixtures thereof, and (b) hydrogen fluoride, such that the reaction effluent from said process is separated in a settling zone into a hydrocarbon phase containing minor amounts of metal pentafluoride and a catalyst phase;
   2. removing at least a portion of the metal pentafluoride from the hydrocarbon phase by contact with a solvent comprising substantially anhydrous liquid hydrogen fluoride, thereby forming a hydrocarbon phase depleted in metal pentafluoride and an extract phase containing hydrogen fluoride and the metal pentafluoride thus removed, the molar ratio of hydrogen fluoride to metal pentafluoride in said extract phase being greater than that desired in said hydrocarbon conversion process, the improvement which comprises maintaining the molar ratio of hydrogen fluoride to metal pentafluoride in the extract phase at the level desired in said hydrocarbon conversion process while inhibiting the deactivation of the catalyst phase by:
   3. combining at least a portion of said extract phase with said catalyst phase in said settling zone to form a catalyst mixture and stripping said mixture with a gas containing molecular hydrogen for a time sufficient to reduce the molar ratio of hydrogen fluoride to metal pentafluoride in said catalyst mixture to the level desired in said hydrocarbon converting step (1); and
   4. passing at least a portion of said stripped catalyst mixture from step (3) to said converting step (1).

2. The process of claim 1 wherein the metal pentafluoride is tantalum pentafluoride.

3. The process of claim 1 wherein the metal pentafluoride removal step (2) is effected at a temperature in the range of from about 0° to about 200° F., at a pressure in the range of from about 20 to about 250 psig, and at a volume ratio of said liquid hydrogen fluoride to the hydrocarbon phase in the range of from about 1:200 to 1:1.

4. The process of claim 1 wherein the molar ratio of hydrogen fluoride to metal pentafluoride in said hydrocarbon converting step (1) ranges from about 1 to 40.

5. The process of claim 1 wherein said hydrocarbon converting step (1) is effected in the presence of hydrogen.

6. The process of claim 5 wherein said hydrocarbon converting step (1) is isomerization and said hydrocarbon feedstock is selected from the group consisting of an acyclic hydrocarbon having at least 4 carbon atoms, an alicyclic hydrocarbon having at least 6 carbon atoms and mixtures thereof.

7. The process of claim 5 wherein in said hydrocarbon converting step (1) said hydrocarbon feedstock is selected from the group consisting of an acyclic hydrocarbon an alicyclic hydrocarbon having at least 5 carbon atoms, an aromatic, hydrocarbon, an alkylaromatic hydrocarbon having at least 6 carbon atoms and mixtures thereof.

8. The process of claim 1 wherein in said hydrocarbon converting step (1) said hydrocarbon feedstock is selected from the group consisting of an acyclic hydrocarbon an alicyclic hydrocarbon having at least 5 carbon atoms, hydrocarbon, an alkylaromatic hydrocarbon having at least 6 carbon atoms and mixtures thereof.

9. The process of claim 1 wherein in said hydrocarbon converting step (1) said hydrocarbon feedstock is selected from the group consisting of i-$C_4$-$C_6$ aliphatic hydrocarbons, $C_5$-$C_{15}$ cycloaliphatic hydrocarbons and mixtures thereof and said hydrocarbon feedstock is reacted with a paraffin having more than 6 carbon atoms.

* * * * *

UNITED STATES PATENT OFFICE
CERTIFICATE OF CORRECTION

PATENT NO. : 4,065,381
DATED : December 27, 1977
INVENTOR(S) : Geoffrey R. Say, William C. Baird, Jr. and Paul W. Kamienski It is certified that error appears in the above-identified patent and that said Letters Patent are hereby corrected as shown below:

At column 6, lines 61-67, the Table should be shown as follows:

|  | Setting Time | |
|---|---|---|
| Hydrogen Stripping | No | Yes |
| Run No. | | |
| 1 | 25 | 24 |
| 2 | 24 | 25 |
| 3 | 21 | 26 |
| 4 | 21 | 25 |

In the (Grant Only) delete Fig. 1 and Fig. 2, as shown on page 2 of the subject patent.

Signed and Sealed this

Thirteenth Day of June 1978

[SEAL]

Attest:

RUTH C. MASON
Attesting Officer

DONALD W. BANNER
Commissioner of Patents and Trademarks